United States Patent [19]

Schoner et al.

[11] Patent Number: 4,914,030
[45] Date of Patent: Apr. 3, 1990

[54] CARBOMYCIN RESISTANCE-CONFERRING GENE, DESIGNATED CARB, FOR USE IN STREPTOMYCES AND OTHER ORGANISMS

[75] Inventors: Brigitte E. Schoner, Zionsville; Janet K. Epp, Indianapolis, both of Ind.

[73] Assignee: Eli Lilly and Company, Indianapolis, Ind.

[21] Appl. No.: 901,334

[22] Filed: Aug. 28, 1986

[51] Int. Cl.[4] .............. C12N 15/00; C12N 1/20; C12N 1/00; C12P 21/00; C12P 21/02; C12P 19/62; C12P 19/34; C12R 1/465; C07K 13/00; C07H 15/12

[52] U.S. Cl. .............. 435/172.3; 435/69.1; 435/34; 435/76; 435/91; 435/172.1; 435/253.5; 435/320; 435/886; 530/350; 536/27

[58] Field of Search ............ 435/76, 91, 172.1, 172.3, 435/253, 255, 256, 320, 886; 536/27; 935/19, 23, 27, 38, 55, 60

[56] References Cited

U.S. PATENT DOCUMENTS 2,902,412 9/1959 Pagano et al. .................. 435/76

OTHER PUBLICATIONS

Benveniste and Davies, 1973, Proc. Natl. Acad. Sci. U.S.A. 70(8): 2276-2280.
Thompson et al., 1980, Nature 286: 525-527.
Fujisawa and Weisblum, 1981, J. Bacteriol. 146(2): 621-631.
Thompson et al., 1982, J. Bacteriol. 151(2): 668-677.
Thompson et al., 1982, J. Bacteriol. 151(2): 678-685.
Thompson et al., 1982, Gene 20: 51-62.
Murakami et al., 1983, J. Antibiotics 36(10): 1305-1311.
Tohyama et al., 1984, J. Antibiotics 37(12): 1736-1737.
Nakano et al., 1984, J. Bacteriol. 157(1): 79-83.
Bibb et al., 1985, Mol. Gen. Genet. 199: 26-36.
Ohnuki et al., 1985, J. Bacteriol. 161(3): 1010-1016.
Distler et al., 1985, FEMS Microbiology Letters 30: 151-154.
Vara et al., 1985, Gene 33: 197-206.
Birmingham et al., 1984, Abstracts of the ASM Conference on Genetics and Molecular Biology of Industrial Microorganisms, Bloomington, Ind., Abstract No. 220.
Uchiyama and Weisblum, 1985, Gene 38: 103-110.

*Primary Examiner*—Thomas G. Wiseman
*Assistant Examiner*—Joan Ellis
*Attorney, Agent, or Firm*—Douglas K. Norman; Leroy Whitaker

[57] ABSTRACT

The carB gene is a novel carbomycin resistance-conferring gene isolated from *Streptomyces thermotolerans* and used to construct a number of cloning vectors for use in Streptomyces and related organisms. One such cloning vector, plasmid pOJ159, can be obtained in *S. griseofuscus* C581 under the accession number NRRL 18090. *S. lividans* and *S. griseofuscus* are the preferred hosts when the carB gene is used to select carbomycin-resistant Streptomyces transformants.

25 Claims, 2 Drawing Sheets

Restriction Site and Function Map of Plasmid pOJ159 pOJ159

Restriction Site and Function Map of Plasmid pOJ159 pOJ159

Restriction Site and Function Map of Plasmid pOJ169

CARBOMYCIN RESISTANCE-CONFERRING GENE, DESIGNATED CARB, FOR USE IN STREPTOMYCES AND OTHER ORGANISMS

SUMMARY OF THE INVENTION

The present invention comprises a novel carbomycin resistance-conferring gene, designated carB, a method for using the carB gene, recombinant DNA cloning vectors that comprise the novel gene, and transformants containing the carbomycin resistance-conferring vectors. *Streptomyces thermotolerans* (ATCC 11416) produces carbomycin, a macrolide antibiotic consisting of a 16-member cyclic lactone and two sugar residues. The antibiotic activity of carbomycin, like that of other macrolides, is due to inhibition of protein synthesis by a mechanism that involves the binding of carbomycin to the ribosome.

The present invention provides carbomycin resistance-conferring cloning vectors for use in Streptomyces and other host cells. The development and exploitation of recombinant DNA technology in Streptomyces depends upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present invention are particularly useful, because the vectors are small, versatile, and can be transformed and selected in a variety of carbomycin-sensitive Streptomyces cells. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics and antibiotic derivatives.

The present invention further provides vectors that enable identification of Streptomyces transformants. After the addition of non-selectable DNA to a vector of the present invention, the modified vector can be transformed into Streptomyces and transformants identified by their carbomycin-resistant phenotype. Because transformation is a relatively low frequency event, such a functional test is a practical necessity for determining which cell(s), of among the millions of cells, has acquired the transforming DNA.

For purposes of the present invention, as disclosed and claimed herein, the following terms are defined below.

ApR—the ampicillin-resistant phenotype or gene conferring same.

carA—a carbomycin resistance-conferring gene of type A.

carB—a carbomycin resistance-conferring gene of type B.

mel—the tyrosinase gene.

Phasmid—a recombinant DNA vector that may act as a phage or as a plasmid.

Recombinant DNA Cloning Vector—any autonomously replicating or integrating agent, including, but not limited to, plasmids, comprising a DNA molecule to which one or more additional DNA segments can be or have been added.

Restriction Fragment—any linear DNA molecule generated by the action of one or more restriction enzymes.

Sensitive Host Cell—a host cell that cannot grow in the presence of a given antibiotic without a DNA segment that provides resistance thereto.

TcR—the tetracycline-resistant phenotype or gene conferring same.

Transformant—a recipient host cell that has undergone transformation.

Transformation—the introduction of DNA into a recipient host cell that changes the genotype and results in a change in the recipient cell.

tsrR—the thiostreption-resistant phenotype or gene conferring same.

BRIEF DESCRIPTION OF THE FIGURES

The figures described below are drawn to scale; however, observed restriction fragment size may vary somewhat from calculated size based on map distances. For some restriction enzymes, such as MboI, only the significant cut sites are shown.

DETAILED DESCRIPTION OF THE INVENTION

Figure 1:
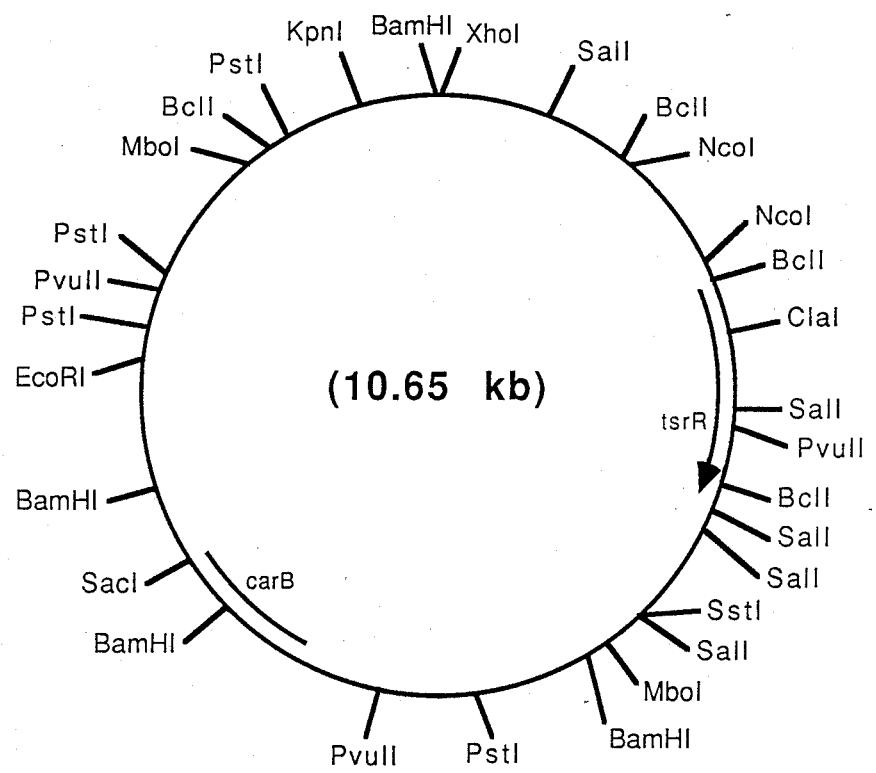
FIG. 1 is a restriction site and function map of plasmid pOJ159.

The present invention concerns a novel carbomycin resistance-conferring gene, designated carB, that is useful as a genetic marker in many organisms. The carB gene is useful in a method for selecting a recombinant DNA-containing host cell that comprises transforming a carbomycin-sensitive host cell with a recombinant DNA vector that codes for expression of the carB gene product and culturing the transformed cell under conditions suitable for selection of carbomycin-resistant transformants. The carB gene can be isolated from plasmid pOJ159 on an ~3.0 kb PstI restriction fragment; plasmid pOJ159 can be isolated from *Streptomyces griseofuscus* C581/pOJ159, a strain deposited and made part of the permanent culture collection of the Agricultural Research Service, Northern Regional Research Center (NRRL), Peoria, IL 61604, under the accession number NRRL 18090. A restriction site and function map of plasmid pOJ159 is presented in FIG. 1 of the accompanying drawings. Plasmid pOJ159 can be isolated from *S. griseofuscus* C581/pOJ159 in substantial accordance with the procedure described in Example 1.

Figure 2:
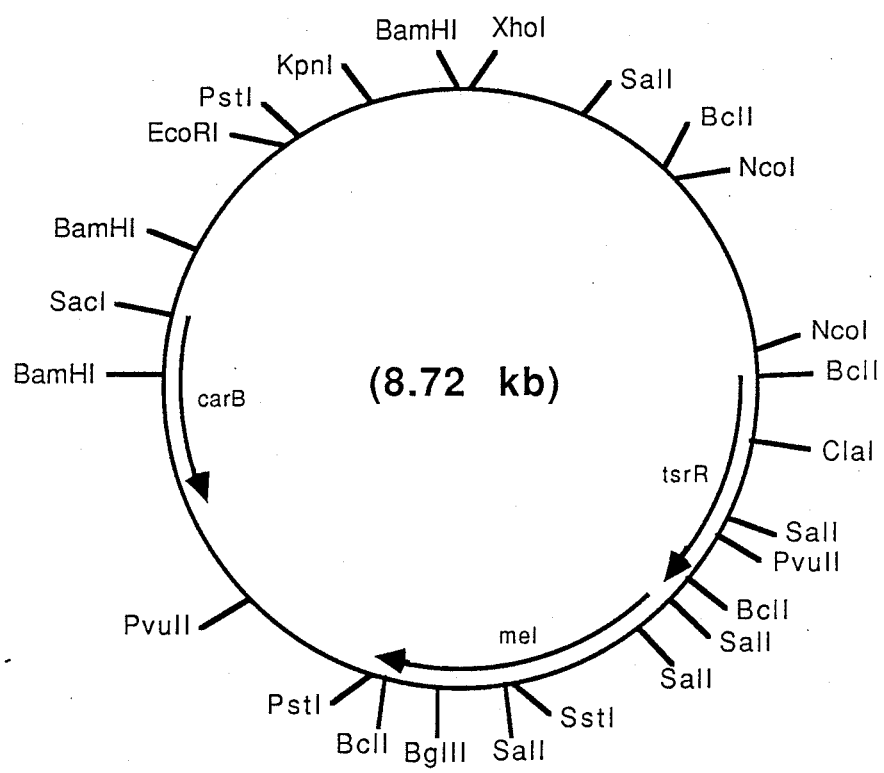
FIG. 2 is a restriction site and function map of plasmid pOJ169.

Plasmid pOJ159 serves as useful starting material for the construction of other vectors that confer carB-mediated carbomycin resistance. For example, the ~3.0 kb PstI, carbomycin resistance-conferring restriction fragment of plasmid pOJ159 was isolated and inserted into PstI-digested plasmid pIJ702 (ATCC 39155) to yield plasmids pOJ169 and pOJ170, which differ only with respect to the orientation of the ~3.0 kb PstI, carbomycin resistance-conferring restriction fragment. The construction protocol for plasmids pOJ169 and pOJ170 is given in Example 2; a restriction site and function map of plasmid pOJ169 is presented in FIG. 2 of the accompanying drawings.

The carB gene was isolated from a carbomycin-producing strain of *Streptomyces thermotolerans* (ATCC 11416). Thus, genomic DNA of *S. thermotolerans* was partially digested with restriction enzyme MboI, and the resulting DNA was inserted into BglII-digested plasmid pIJ702 to yield a number of carB-containing plasmids, including plasmid pOJ159. Because the carB gene was isolated from *S. thermotolerans*, the carB gene functions in *S. thermotolerans*, but the carB gene with its natural promoter also functions in other organisms.

The vectors of the present invention have also been used to transform *Streptomyces lividans* TK23 (NRRL 15826) and *Streptomyces griseofuscus* C581 (ATCC 23916) to carbomycin resistance, as described in Example 3. Thus, the carB gene can be used to transform a variety of carbomycin-sensitive Streptomyces strains to carbomycin resistance. In organisms naturally sensitive to macrolide antibiotics, including carbomycin, the carB gene can be used as a genetic marker. In organisms that produce one or more macrolide antibiotics yet are sensitive to low levels of macrolide antibiotic, the vectors of the present invention can be used to increase or augment the organism's natural resistance. The following Tables present a representative sampling of various antibiotic-producing organisms in which the carB gene can be used.

TABLE I

Aminocyclitol Antibiotic-Producing Organisms

| Organism | Antibiotic |
|---|---|
| various species Micromonospora | various aminocyclitols |
| various species Saccharopolyspora | gentamycins |
| various species Streptomyces | various aminocyclitols |
| albogriseolus | neomycins |
| albus var. metamycinus | metamycin |
| aquacanus | N-methyl hygromycin B |
| atrofaciens | hygromycins |
| bikiniensis | streptomycin |
| bluensis var. bluensis | bluensomycin |
| canus | ribosyl paromamine |
| catenulae | catenulin |
| chrestomyceticus | aminosidine |
| crystallinus | hygromycin A |
| erythrochromogenes var. narutoensis | streptomycin |
| eurocidicus | A16316-C |
| fradiae | hybrimycins and neomycins |
| fradiae var. italicus | aminosidine |
| galbus | streptomycin |
| griseus | streptomycin |
| griseoflavus | MA 1267 |
| hofuensis | seldomycin complex |
| hygroscopicus | hygromycins, leucanicidin, and hygrolidin |
| hygroscopicus forma glebosus | glebomycin |
| hygroscopicus var. limoneus | validamycins |
| hygroscopicus var. sagamiensis | spectinomycin |
| kanamyceticus | kanamycin A and B |
| kasugaensis | kasugamycins |
| kasugaspinus | kasugamycins |
| lavendulae | neomycin |
| lividus | lividomycins |
| mashuensis | streptomycin |
| microsporeus | SF-767 |
| netropsis | LL-AM31 |
| noboritoensis | hygromycins |
| olivaceus | streptomycin |
| olivoreticuli var. cellulophilus | destomycin A |
| poolensis | streptomycin |
| rameus | streptomycin |
| ribosidificus | SF733 |
| rimofaciens | destomycin A |
| rimosus forma paromomycinus | paromomycins and catenulin |
| spectabilis | spectinomycin |

TABLE I-continued

Aminocyclitol Antibiotic-Producing Organisms

| Organism | Antibiotic |
|---|---|
| tenebrarius | tobramycin and apramycin |
| Streptoverticillium flavopersicus | spectinomycin |

TABLE II

Ansamycin Antibiotic-Producing Organisms

| Organism | Antibiotic |
|---|---|
| Micromonospora various species | various ansamycins |
| Nocardia mediterranei | rifamycin |
| Streptomyces | |
| collinus | ansatrienes and napthomycins |
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotrienes |
| sp. E88 | mycotrienes |
| spectabilis | streptovaricins |
| tolypophorous | tolypomycin |

TABLE III

Anthracycline and Quinone Antibiotic-Producing Organisms

| Organism | Antibiotic |
|---|---|
| Streptomyces | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromogenes | arugomycin |

TABLE IV

β-Lactam Antibiotic-Producing Organisms

| Organism | Antibiotic |
|---|---|
| Agrobacterium | various β-lactams |
| Cephalosporium acremonium | penicillins and cephalosporins |
| Chromobacterium | various β-lactams |
| Gluconobacter | various β-lactams |
| Nocardia | |
| lactamadurans | cephamycin C |
| uniformis | nocardicin |
| Penicillium chrysogenum | various penicillins and other β-lactams |
| Serratia | various β-lactams |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |

TABLE IV-continued

β-Lactam Antibiotic-Producing Organisms

| Organism | Antibiotic |
|---|---|
| cinnamonensis | cephamycin A and B |
| clavuligerus | PA-32413-I, cephamycin C, A16886A, penicillins cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxycephalosporin C |
| lipmanii | cephamycin, penicillin N, 7-methoxycephalosporin C, A16884, MM 4550, MM 13902 |
| olivaceus | epithienamycin F, MM 4550, and MM 13902 |
| panayensis | C2081X and cephamycin A and B |
| rochei | cephamycin A and B |
| sioyaensis | MM 4550 and MM 13902 |
| sp. OA-6129 | OA-6129A |
| sp. KC-6643 | carpetimycin A |
| viridochromogenes | cephamycin A and B |
| wadayamensis | WS-3442-D |

TABLE V

Macrolide, Lincosamide, and Streptogramin Antibiotic-Producing Organisms

| Organism | Antibiotic |
|---|---|
| Micromonospora | |
| rosaria | rosaramicin |
| Streptomyces | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |

TABLE V-continued

Macrolide, Lincosamide, and Streptogramin Antibiotic-Producing Organisms

| Organism | Antibiotic |
|---|---|
| hygroscopicus subsp. aureolacrimosus | milbemycins |
| kitastoensis | leucomycin $A_3$ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin $A_3$ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE VI

Miscellaneous Antibiotic-Producing Streptomyces

| Antibiotic Type | Streptomyces Species | Antibiotic |
|---|---|---|
| amino acid analogues | sp. | cycloserine |
| cyclopentane ring-containing | coelicolor | methylenomycin A |
| | erythrochromogenes | sarkomycin |
| | Kasugaensis | aureothricin and thiolutin |
| | violaceoruber | methylenomycin A |
| nitro-containing | venezuelae | chloramphenicol |
| polyenes | griseus | candicidin |
| | nodosus | amphotericin B |
| | noursei | nystatin |
| tetracyclines | aureofaciens | tetracycline, chlortetracycline, demethyltetracycline, and demethylchlortetracycline |
| | rimosus | oxytetracycline |

TABLE VII

Nucleoside Antibiotic-Producing Organisms

| Organism | Antibiotic |
|---|---|
| Corynebacterium michiganese pv. rathayi | tunicamycin analogues |
| Nocardia candidus | pyrazofurin |
| Streptomyces | |
| antibioticus | ara-A |
| chartreusis | tunicamycin |
| griseoflavus var. thuringiensis | streptoviridans |
| griseolus | sinefungin |
| lysosuperificus | tunicamycin |

TABLE VIII

Peptide Antibiotic-Producing Organisms

| Organism | Antibiotic |
|---|---|
| Actinoplanes | |
| *missouriensis* | actaplanin |
| *teichomyceticus* | teicoplanin |
| Bacillus | |
| various species | bacitracin, polymixin, and colistin |
| Nocardia | |
| *candidus* | A-35512 and avoparcin |
| *lurida* | ristocetin |
| *orientalis* | vancomycin |
| Streptomyces | |
| *antibioticus* | actinomycin |
| *aureus* | thiostrepton |
| *canus* | amphomycin |
| *eburosporeus* | LL-AM374 |
| *haranomachiensis* | vancomycin |
| *pristinaespiralis* | pristinamycin |
| *roseosporus* | lipopeptides, such as A21978C |
| *toyocaensis* | A47934 |
| *virginiae* | A41030 |

TABLE IX

Polyether Antibiotic-Producing Organism

| Organism | Antibiotic |
|---|---|
| Actinomadura | |
| various species | various polyethers |
| *oligosporus* | A80190 |
| Dactylosporangium | |
| various species | various polyethers |
| Nocardia | |
| various species | various polyethers |
| Streptomyces | |
| *albus* | A204, A28695A and B, and salinomycin |
| *aureofaciens* | narasin |
| *bobili* | A80438 |
| *cacaoi* var. *asoensis* | lysocellin |
| *chartreusis* | A23187 |
| *cinnamonensis* | monensin |
| *conglobatus* | ionomycin |
| *eurocidicus* var. *asterocidicus* | laidlomycin |
| *flaveolus* | CP38936 |
| *gallinarius* | RP 30504 |
| *griseus* | grisorixin |
| *hygroscopicus* | A218, emericid, DE3936, A120A, A28695A and B, etheromycin, and dianemycin |
| *lasaliensis* | lasalocid |
| *longwoodensis* | lysocellin |
| *mutabilis* | S-11743a |
| *pactum* | A80438 |
| *ribosidificus* | Ionomycin |
| *violaceoniger* | nigericin |
| Streptoverticillium | |
| various species | various polyethers |

As the carB gene was isolated from *Streptomyces thermotolerans*, the carB gene should function in most Streptomyces species. Yet even if the intact carB gene failed to express in a given organism, such as E. coli, because, for example, the Streptomyces promoter failed to function in that organism, the carB protein-coding sequence of the present invention could be ligated to a DNA containing an appropriate promoter and ribosome-binding site to achieve expression of the carB gene.

Plasmid pOJ159 contains the complete carB gene: (1) a promoter that directs transcription of the protein-coding sequence; (2) a sequence that, when transcribed into mRNA, directs translation of the transcript; (3) a protein-coding sequence; and (4) a transcription terminator. Each of these elements is independently useful and can, through the techniques of recombinant DNA technology, be used to form recombinant genes of great variety. The DNA sequence of the carB gene, depicted below, reveals the location of the carB coding sequence and thus allows one to position other promoters, for example, the trp, lpp, and lac promoters of *E. coli* and the veg promoter of Bacillus, in reading phase with the carB coding sequence. By choosing the proper promoter, one can construct vectors that drive expression of the carB gene product in any given host cell. The promoter of the carB gene is useful in its own right. The promoter and other regulatory elements of the carB gene can be linked to the coding sequence of a non-carbomycin antibiotic biosynthetic gene to prepare a hybrid antibiotic pathway gene that functions in another Streptomyces species to yield a hybrid antibiotic. Thus, the individual elements of the gene on the plasmids described herein comprise important components of the present invention.

The sequence of the carB gene was obtained by first cloning the ~3 kb carbomycin resistance-conferring PstI restriction fragment of plasmid pOJ159 into PstI-digested plasmid SP64 to yield plasmids pOJ168 and pOJ168.1, which differ only with respect to the orientation of the ~3 kb PstI restriction fragment. Plasmid SP64 is a "riboprobe" vector marketed by Promega Biotec, 2800 S. Fish Hatchery Road, Madison, Wis. 53711. The pertinent region of plasmid pOJ168 was then sequenced (Maxam and Gilbert, 1980, Methods in Enzymology 65:449–560 and Sanger et al., 1977, Proc. Natl. Acad. Sci. 74:5463–5467) to determine the nucleotide sequence of the carB gene. The sequence of the carB gene is depicted below, beginning with the 5' end upstream of the coding sequence. Only the sequence of the coding strand of the carB gene is depicted; the sequence of the non-coding strand can be obtained using the well-known rules of base-pairing: A pairs with T, and C pairs with G. The amino acid residue sequence of the carB gene product is also depicted below, beginning with the amino-terminal end; each amino acid residue is located below the DNA encoding that residue. Both the DNA and amino acid residue sequences are numbered to facilitate discussion.

NUCLEOTIDE SEQUENCE OF THE carB GENE AND AMINO ACID RESIDUE SEQUENCE OF THE carB GENE PRODUCT

```
                 10          20          30          40
5'-CGCTGGACTG CCGCCCGGTT TTGAGCAGGC ATTTCGCCCG 50          60          70          80
   TCCGCCCGCA CGGCGGGGCC AGCCACGGGC CGGTGTCCGC 90         100         110         120
   CGCCGGCGCC GCGCCACCCC CACGGCCGCA TCCCGTACCC 130         140         150         160
   GGGCTGCGGC CGCTTCGGGT TGTCCTCTGC CGCGGCTTGA 170         180         190         200
   TTTCACCTCC CCGGGGGGTG TGCGTAGTGG CAGCGAAGGT 210         220         230         240
   AAAGGGAGGT TAAGGTGTCC GTCCGCCGGG GTTCCTGTAC 250         260         270         280
   GTAATGGCTG CGCTCCTGAA GCGCATACTT AGGAGACGCA 290         300         310         320         330
TGGCTGAAAA GAGGTCAGGA CGCGGGCGC ATG GCC GCA GCG CGT ACA ACC GGA GCT
                                  MET ALA ALA ALA ARG THR THR GLY ALA
                                                                  5

340          350          360          370          380
CAG TCG CGT AAA ACG GCA CAG CGG TCG GGC CGG AGT GAG GCT GAC CGT
GLN SER ARG LYS THR ALA GLN ARG SER GLY ARG SER GLU ALA ASP ARG
 10              15                      20                  25

390          400          410          420          430
AGA AGA AGA GTC CAC GGG CAG AAT TTC CTC GTC GAC CGG GAA ACA GTA
ARG ARG ARG VAL HIS GLY GLN ASN PHE LEU VAL ASP ARG GLU THR VAL
                 30                      35                  40

440          450          460          470          480
CAA CGG TTT GTG CGT TTC GCC GAT CCG GAC CCC GGG GAG GTC GTT CTC
GLN ARG PHE VAL ARG PHE ALA ASP PRO ASP PRO GLY GLU VAL VAL LEU
             45                      50                  55

490          500          510          520
GAG GTC GGT GCC GGT AAT GGT GCG ATC ACG CGC GAG CTG GCG CGA TTA
LEU GLU VAL GLY ALA GKY ASN GLY ALA ILE THR ARG GLU LEU ALA ARG
             60                   65                  70

530          540          550          560          570
TGC CGA CGA GTG GTG GCG TAT GAG ATC GAC CGG CAC TTC GCG GACCGA
CYS ARG ARG VAL VAL ALA TYR GLU ILE ASP ARG HIS PHE ALA ASP ARG
 75                   80                  85

580          590          600          610          620
TTA CGT GAG GCG ACC GCC GAG GAT CCG CGG ATC GAG GTC GTC GCC GGC
LEU ARG GLU ALA THR ALA GLU ASP PRO ARG ILE GLU VAL VAL ALA GLY
 90                   95                     100                 105

630          640          650          660          670
GAC TTC CTG AAG ACC TCG CAG CCC AAG GTC CCG TTC TCC GTG GTC GGC
ASP PHE LEU LYS THR SER GLN PRO LYS VAL PRO PHE SER VAL VAL GLY
                 110                     115                 120

680          690          700          710          720
AAC ATC CCG TTC GGC AAC ACC GCG GAC ATA GTG GAC TGG TGC CTG AAC
ASN ILE PRO PHE GLY ASN THR ALA ASP ILE VAL ASP TRP CYS LEU ASN
             125                     130                 135

730          740          750          760
GCG CGG CGG CTG CGT ACG ACC ACC CTG GTC ACC CAG CTC GAA TAC GCC
ALA ARG ARG LEU ARG THR THR THR LEU VAL THR GLN LEU GLU TYR ALA
             140                     145                 150

770          780          790          800          810
CGC AAG CGC ACC GGC GGC TAT CGG CGC TGG TCA CGG CTC ACC GTC GCC
ARG LYS ARG THR GLY GLY TYR ARG ARG TRP SER ARG LEU THR VAL ALA
 155                     160                     165

820          830          840          850          860
ACC TGG CCC GAG GTG GAG TGG CGG ATG GGC GAG CGG ATC AGC CGC CGC
THR TRP PRO GLU VAL GLU TRP ARG MET GLY GLU ARG ILE SER ARG ARG
170                  175                     180                 185
```

```
                870           880           890           900           910
        TGG TTC CGG CCC GTC CCC GCC GTC GAC TCC GCG GTA CTG CGA CTG GAA
        TRP PHE ARG PRO VAL PRO ALA VAL ASP SER ALA VAL LEU ARG LEU GLU
                    190                   195                   200

920           930           940           950           960
        CGG CGA CCG GTG CCG CTG ATC CCA CCO GGT CTG ATG CAC GAC TTC CGG
        ARG ARG PRO VAL PRO LEU ILE PRO PRO GLY LEU MET HIS ASP PHE ARG
                    205                   210                   215

970           980           990          1000
        GAC CTG GTG GAG ACC GGG TTC ACG GGA AAG GGC GGT TCG CTG GAC GCC
        ASP LEU VAL GLU THR GLY PHE THR GLY LYS GLY GLY SER LEU ASP ALA
                    220                   225                   230

1010          1020          1030          1040          1050
        TCG CTG CGC CGG CGC TTC CCG GCC CGG CGG GTG GCC GCC GGG TTC CGC
        SER LEU ARG ARG ARG PHE PRO ALA ARG ARG VAL ALA ALA GLY PHE ARG
                    235                   240                   245

1060          1070          1080          1090          1100
        AGG GCC CGC CTG GAG CAG GGC GTG GTC GTC GCC TAC GTC ACC CCG GGC
        ARG ALA ARG LEU GLU GLN GLY VAL VAL VAL ALA TYR VAL THR PRO GLY
        250                 255                   260                   265

1110          1120          1130          1140          1150
        CAA TGG ATC ACA CTC TTC GAG GAA CTC CAC GGG CGC TGA CGCACAC
        GLN TRP ILE THR LEU PHE GLU GLU LEU HIS GLY ARG
                    270                   275

1160          1170          1180          1190          1200
        CGGTGCGGGG CGCGCCCGAG GGCGCGCCCC GCACCGGTCG TCCCGCGTCG 1210          1220          1230          1240          1250
        GCTACGGAGT GCCGGACGGG GCGGGTTCGG ACCTGGGTGT CGAGCCGGCG

1260
        TCCGGGGACC-3'
``` wherein

A is deoxyadenyl, G is deoxyguanyl, C is deoxycytidyl, T is thymidyl, ALA is an alanine, ARG is an arginine, ASN is an asparagine, ASP is an aspartic acid, CYS is a cysteine, GLN is a glutamine, GLU is a glutamic acid, GLY is a glycine, HIS is a histidine, ILE is an isoleucine, LEU is a leucine, LYS is a lysine, MET is a methionine, PHE is a phenylalanine, PRO is a proline, SER is a serine, THR is a threonine, TRP is a tryptophan, TYR is a tyrosine, and VAL is a valine.

There is some uncertainty as to the precise location of the beginning of the carB coding region, because there are three in-frame methionine codons (ATG) located within the first 100 bp of the open-reading frame at positions 244, 280 and 310. Translation from these sites would generate proteins with 299, 287 and 277 amino acids, respectively. Only the third of the three ATG codons (at position 310) is preceeded by an appropriately spaced Shine-Dalgarno (SD) 5'-AGGA-3' with a window size of 9 nucleotides. A second SD sequence (GAGG) occurs 13 nucleotides upstream from this ATG codon, but a window size of 13 bp places this SD sequence further upstream than has been generally observed. Similarly, a SD sequence (GGAG), located 4 nucleotides upstream from the ATG codon at position 280 is closer than what has been generally observed. No SD sequence is associated with the ATG codon at position 244. Although a GTG condon could be utilized for translation initiation, this seems less likely as the first GTG codon in the sequence appears at position 442 and has no associated SD sequence. Although not wishing to be bound by theory, we believe translation of the carB open reading frame most likely begins at position 310; therefore, we have depicted the start of the amino acid residue sequence of carB at position 310.

Those skilled in the art will recognize that the carB sequence depicted above and deposited under accession number NRRL 18090 can be used to prepare synthetic or natural DNA probes for use in obtaining other RNA methylase-encoding DNA segments and macrolide, lincosamide, and streptogramin (MLS) resistance-conferring genes. In addition, due to the diversity of Streptomyces thermotolerans strains both in nature and also in the laboratory, there will be a variety of allelic variants of the carB gene that can be readily isolated given the sequence of the carB gene depicted above. These allelic variants, which encode gene products with an amino acid residue sequence that differs from that of the carB gene product in only a few residues, are equivalent to the carB gene of the present invention.

The DNA sequence past the termination codon (TGA), at position 1141, contains a GC-rich inverted repeat that potentially can form a very stable hairpin-loop structure, herein defined as a transcription terminator. The stem in this structure, which roughly comprises the sequence from position 1141 to position 1194, contains 18 perfectly matched base pairs and a calculated ΔG of −70 kcals. These structures conventionally represent transcription terminators and can impart stability upon the transcripts and play a regulatory role. The structure of the hairpin-loop structure is depicted below.

```
              A G
            C     G
            C—G
            C—G
            G—C
            C—G
            G—C
            C—G
            G—C
            G—C
            G—C
            G—C
            C—G
            G—C
            T—A
            G—C
            G—C
            C—G
            C—G
      5'-TGACGCACA    TCGTCCC-3'
```

Restriction fragments containing the termination sequence depicted above can be conveniently isolated from plasmid pOJ159, or can be synthesized using manual or automated techniques, and used to prepare recombinant genes for expression in Streptomyces.

Although the above-described vectors comprise the Streptomyces replicon derived from plasmid pIJ702, a variety of known Streptomyces replicons can be used to construct equally useful vectors with different host ranges. Table X is an illustrative, but not comprehensive, listing of Streptomyces plasmids from which Streptomyces replicons can be obtained. Those skilled in the art recognize that, so long as the replicon function is not disrupted, all or part of the plasmids can be used to construct vectors that contain the carB gene of the present invention. The plasmid-containing host and depository accession number are also listed in Table X.

TABLE X

Streptomyces Plasmids

| Plasmid | Host | Accession Number |
|---------|------|------------------|
| SCP2 | *Streptomyces coelicolor* A3(2) | NRRL 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| PUC3 | Streptomyces 3022A | NRRL 11441 |
| SLP1 | *Streptomyces lividans* | NCIB* 11417 |
| pNM100 | *Streptomyces virginiae* | NRRL 15156 |
| pEL103 | *Streptomyces granuloruber* A399 12.13/pEL103 | NRRL 12549 |
| pIJ702 | *Streptomyces lividans* | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

Restriction fragments used to construct vectors illustrative of the present invention can be conventionally modified to facilitate ligation. For example, molecular linkers can be provided to a particular carbomycin resistance gene-containing restriction fragment or to DNA comprising vector replication or integration functions. Thus, specific sites for subsequent ligation can be conveniently constructed. In addition, the various carbomycin resistance gene-containing restriction fragments, origin of replication, or sequences that provide for chromosomal integration of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that a given carbomycin resistance gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular carbomycin resistance gene-containing restriction fragment.

Of course, the carB gene can be used to construct vectors other than plasmids. Phage φC31 is a well-known Streptomyces phage that is an excellent source of starting material for constructing integrative carbomycin resistance-conferring vectors that further exemplify the present invention. A derivative of phage φC31, phasmid pKC331, is especially preferred for constructing such integrating vectors and can be obtained from *E. coli* K12 BE447/pKC331 (NRRL B-15828). φC31-type phages are integrative vectors and can be readily modified to incorporate the carB gene and thus confer carbomycin resistance to Streptomyces.

The vectors of the present invention comprise a Streptomyces replicon and a carbomycin resistance-conferring restriction fragment. Because amplification and manipulation of plasmids is done faster and more efficiently in *E. coli* than in Streptomyces, it is convenient to add DNA sequences that also allow for replication in *E. coli*. Thus, the addition of functional replicon-containing and antibiotic resistance-conferring restriction fragments from *E. coli* plasmids such as, for example, pBR322, pACYC184, pBR325, pBR328, and the like is highly advantageous and adds to the general utility of the present illustrative vectors.

The carB gene confers resistance to carbomycin and other antibiotics. In *Streptomyces griseofuscus*, carB confers resistance to carbomycin, spiramycin, rosamycin, lincomycin, and vernamycin B. In *S. lividans*, carB additionally confers resistance to erythromycin and oleandomycin. Inducible resistance to macrolide antibiotics, such as tylosin, carbomycin, and erythromycin, in Gram-positive bacteria (such as Staphylococcus, Streptomyces, Streptococcus, and Bacillus) is associated with co-resistance to lincosamide and streptogramin-type B antibiotics; this multi-drug-resistant phenotype is called the MLS-resistant phenotype (Fujisawa and Weisblum, 1981, J. Bacteriol. 146:621–631). In *Staphylococcus aureus*, the MLS-resistant phenotype arises upon specific methylation of an adenine residue in 23S ribosomal RNA (rRNA) resulting in the formation of $N^6$-dimethyladenine. MLS-resistance in *Streptomyces erythreus*, an erythromycin producer, arises upon $N^6$-dimethylation of a single adenine residue in 23S rRNA. Thompson et al. cloned a *S. erythreus* gene, ermE, that conferred erythromycin resistance in S. lividans via a mechanism that generated $N^6$-dimethyladenine in 23S rRNA. The carB gene may encode a rRNA methylase, because of the extensive amino acid sequence homology between the RNA methylase encoded by the ermE gene and the protein encoded by carB. However, the carB gene confers a modified MLS-resistant phenotype, and Table XI, below, presents the results of disc-sensitivity assays, which demonstrate that the carB gene confers resistance to a number of antibiotics. The results presented in Table XI are based on uninduced culture conditions. The carB gene can confer resistance to a greater variety of MLS antibiotics, such as tylosin, when cells containing the carB gene are cultured under inducing conditions prior to selection with antibiotic. Inducing conditions are achieved by exposing the cells to subinhibitory concentrations of certain macrolide antibiotics and other antibiotics that bind to the 50S subunit of the ribosomes. Different species of Streptomyces will exhibit different induction patterns.

TABLE XI

| | Antibiotic Resistance Pattern | | | | |
|---|---|---|---|---|---|
| | S. | S. griseofuscus | | S. lividans | |
| Antibiotic[a] | thermotolerans | pIJ702 | pOJ159 | pIJ702 | pOJ159 |
| erythromycin | 23 | R[b] | R | 20 | R[b,c] |
| oleandomycin | 15 | R | R | 15 | R |
| carbomycin | R | 26 | R[b] | 15(20[c]) | R |
| spiramycin | R | 20 | R | 12 | R |
| tylosin | 16 | 24 | 18 | 16 | 11[c] |
| rosamycin | R[b] | 37 | 11[c] | 11[c] | R |
| lincomycin | R | 13 | R | 12 | R |
| vernamycin B | R[b] | 16 | R[b] | 11[c] | R[b,c] |

[a]20 μg of antibiotic per disc; numbers refer to zone diameters; R indicates no zone.
[b]small zone of growth inhibition.
[c]turbid zone.

The relatively large zones of inhibition of growth around the discs show that *Streptomyces griseofuscus* is quite sensitive to MLS antibiotics, except for erythromycin and oleandomycin. In the presence of pOJ159, the zone sizes are considerably smaller or absent, because of increased resistance to these antibiotics as a result of expression of the carB gene. Rosamycin gave a turbid zone that is due to inducible or partial resistance to rosamycin. The small, but clearly discernable zones around vernamycin and carbomycin show that these antibiotics cause inhibition of growth at lower concentrations than do the other antibiotics tested. The minimal concentration of carbomycin that inhibits growth is given in Table XII, below. Resistance to erythromycin and oleandomycin was analysed in *S. lividans* because this strain is sensitive to these antibiotics. As can be seen in Table XI, the *S. lividans* transformants are resistant to erthromycin and oleandomycin even though *S. thermotolerans* is sensitive to these antibiotics.

As can be seen from Tables XI and XII, the level of macrolide antibiotic required to observe growth inhibition of a sensitive strain varies and depends on the particular antibiotic, host strain, and growth conditions. Those skilled in the art will recognize that the precise experimental conditions, including the preferred macrolide antibiotic concentration, for using the carB gene for purposes of selection can be readily determined by empirical methods. A preferred procedure for determining an organism's sensitivity to carbomycin utilizes antibiotic-gradient plates, as exemplified in Table XII. Disc-sensitivity assays can also be used to determine an organism's sensitivity to carbomycin, as exemplified in Table XI. The vectors of the present invention can increase the endogenous resistance to carbomycin by about 100 fold. Variations in this increase are expected when different promoters are used to drive expression of the carB gene.

TABLE XII

| Strain | MIC (μg/ml) carbomycin[a] |
|---|---|
| S. griseofuscus | 0.5 |
| S. griseofuscus/pIJ702 | 0.5 |
| S. griseofuscus/pOJ159 | 50 |
| S. thermotolerans | >1000 |

[a]values were determined on antibiotic gradient plates (Szybalski. 1952. Science 116: 46–48)

*Streptomyces thermotolerans* contains two carbomycin resistance-conferring genes, designated carA and carB. The level of carbomycin resistance in the *S. griseofuscus* transformants was lower than in *S. thermotolerans*, because the two carbomycin resistance genes act in concert to cause high-level resistance in the antibiotic-producing organism. Alternatively, carB may not be expressed as efficiently in *S. griseofuscus* as in *S. thermotolerans*. The carA gene is disclosed and claimed in, Epp et al., U.S. patent application Ser. No. 901,240, attorney docket No. X-6935, filed herewith at even date.

The recombinant DNA cloning vectors of the present invention have broad utility and help fill the need for suitable cloning vehicles for use in Streptomyces and related organisms. Moreover, the ability of the present vectors to confer carbomycin resistance provides a functional means for selecting transformants. This is important because of the practical necessity for determining and selecting the particular cells that have acquired vector DNA in a transformation procedure.

Additional DNA segments, that lack functional tests for their presence, can also be inserted into the present vectors, and transformants containing the non-selectable DNA can be isolated by selection for carbomycin resistance. Such non-selectable DNA segments can be inserted at any site, except within regions necessary for plasmid function and replication or within the carB gene, and include, but are not limited to, genes that specify antibiotic modification enzymes and regulatory genes of all types.

More particularly, a non-selectable DNA segment that comprises a gene is inserted into a plasmid such as, for example, plasmid pOJ169 at the central ClaI restriction site of the thiostrepton resistance gene. Such an insertion inactivates the thiostrepton resistance gene and thus allows for the easy identification of transformants containing the recombinant plasmid. This is done by first selecting for carbomycin resistance and, secondarily, identifying those carbomycin-resistant transformants that are not resistant to thiostrepton. Therefore, the ability to select for carbomycin resistance in Streptomyces and related cells allows for the efficient isolation of the relatively few cells that contain the particular non-selectable DNA of interest.

The functional test for carbomycin resistance, described above, is also used to locate DNA segments that act as control elements and direct expression of an individual antibiotic resistance-conferring gene. Such segments, including, but not limited to, promoters, attenuators, repressors, inducers, ribosome-binding sites, and the like, are used to control the expression of other genes in Streptomyces and related organisms.

The carbomycin resistance-conferring vectors of the present invention are also useful for ensuring that linked DNA segments are stably maintained in host cells over many generations. These genes or DNA fragments, covalently linked to the carbomycin resistance-conferring DNA and propagated in Streptomyces, are maintained by exposing the transformants to levels of carbomycin toxic to non-transformed cells. Therefore, transformants that lose the vector, and consequently lose any covalently linked DNA, cannot grow and are eliminated from the culture. Thus, the vectors of the present invention can stabilize and maintain DNA sequences of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Tobramycin, Erythromycin, and the like. The present invention also provides selectable vectors that are useful for cloning, characterizing, and reconstructing DNA sequences that code for: commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to, DNA that codes for enzymes that catalyze synthesis of derivatized antibiotics such as, for example, Streptomycin, Cephalosporin, Tylosin, Actaplanin, Narasin, Monensin and Erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 at temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pOJ159

A. Culture of *Streptomyces griseofuscus* C581/pOJ159

About $10^8$ spores of *Streptomyces griseofuscus* C581/pOJ159 (NRRL 18090) are inoculated into 10 ml of TSB medium (Trypticase Soy Broth*) containing 25 µg/ml thiostrepton and grown at 29° C. until the culture is in early stationary phase. The culture was then homogenized, and 5 ml of the homogenized culture were used to inoculate 100 ml of TSB also containing thiostrepton. The 100 ml of culture were incubated at 29° C. until the *Streptomyces griseofuscus* C581/pOJ159 cells reached stationary phase.

*TSB is made at 30 g/l and is obtained from Baltimore Biological Laboratories (BBL), P.O. Box 243, Cockeysville, Md. 21031.

B. Plasmid Isolation

The cells were collected and washed once with a 10.3% sucrose solution. The cells were then suspended in 24 ml of 10.3% sucrose, and 6 ml of 5X lysozyme solution (125 mM Tris-HCl, pH=8; 125 mM Na$_2$EDTA, pH=8; 10 mg/ml lysozyme; and 10.3% sucrose) were added. The solution was mixed and then incubated at 30° C. for 30–60 minutes, and then, about 18 ml of a solution that was 0.3M NaOH, 1% SDS, and prewarmed to 50° C. were added, mixed and the resulting mixture incubated at 80° C. for 10 minutes. The mixture was then cooled to room temperature, and 12 ml of a solution made by mixing 500 g phenol and 500 g CHCl$_3$ in 200 ml H$_2$O were added and mixed well with the cell-extract. The phases were separated by centrifugation at 6000–8000 rpm for 10 minutes; approximately 45 ml of the resulting upper phase were transferred to a clean bottle.

Next, 4.5 ml of 3M NaOAc and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 10 ml of TE buffer (10 mM Tris-HCl, pH=8, and 1 mM EDTA) containing 9.5 g of CsCl. About 1 ml of a 5 mg/ml solution of ethidium bromide was added to the solution to bring the final volume to 12.5 ml. The solution was then centrifuged at 52,000 rpm for 48 hours at 20° C. in a Beckman Ti-75 fixed-angle rotor. The fraction containing the plasmid band was extracted 5 times with isopropanol saturated with 20X SSC (0.3M NaCl and 0.3M NaCitrate) to remove the ethidium bromide. After the extractions, the sample was dialyzed against 1000 volumes of H$_2$O and then against 1500 volumes of TE-buffer. The procedure yields about 100 µg of plasmid pOJ159 DNA at a concentration of ~0.2 µg/µl and is stored at 4° C. A restriction site and function map of plasmid pOJ159 is presented in FIG. 1 of the accompanying drawings.

EXAMPLE 2

Construction of Plasmids pOJ169 and pOJ170

*Streptomyces lividans*/pIJ702 (ATCC 39155) was cultured and plasmid pIJ702 isolated in substantial accordance with the teaching of Example 1. Thiostrepton selection (25 µg/ml) was used to ensure plasmid pIJ702 maintenance. The ~100 µg of plasmid pIJ702 DNA obtained were suspended in 5 ml of TE and stored at 4° C.

About 10 µg (100 µl) of plasmid pIJ702 DNA were added to 13 µl of 10X PstI buffer (500 mM Tris-HCl, pH=7.5; 0.5M NaCl; and 100 mM MgCl$_2$), 14 µl of H$_2$O, and 3 µl (~45 units; unit definitions herein correspond to those of New England Biolabs, 32 Tozer Road, Beverly, Mass. 01915-9990, unless otherwise indicated) of restriction enzyme PstI. The resulting reaction was incubated at 37° C. for two hours. The reaction mixture was extracted with 100 µl of a 1:1 solution of phenol:chloroform and then with 100 µl of chloroform. The PstI-digested DNA was collected by adjusting the sodium acetate (NaOAc) concentration of the reaction mixture to 0.30M, adding two volumes of ethanol, chilling the reaction mixture to −70° C., and centrifuging to pellet the precipitated DNA. The pellet of PstI-digested plasmid pIJ702 DNA was resuspended in 50 μl of TE buffer.

About 10 μg of plasmid pOJ159 in 100 μl of TE buffer were added to 13 μl of 10X PstI buffer, 13 μl of H₂O and 4 μl (~60 units) of restriction enzyme PstI. The resulting reaction was incubated at 37° C. for 2 hours.

The PstI-digested plasmid pOJ159 DNA was then electrophoresed on a 1% agarose gel until the desired ~3.0 kb PstI restriction fragment was clearly separated from the other digestion products. Visualization of the electrophoresed DNA was accomplished by staining the gel in a dilute solution (0.5 μg/ml) of ethidium bromide and exposing the stained gel to longwave UV light. After the desired fragment was located, a small slit was made in the gel in front of the fragment, and a small piece of Schleicher and Schuell (Keene, N.H. 03431) NA-45 DEAE membrane was placed in the slit. Upon further electrophoresis, the ~3.0 kb PstI restriction fragment was non-covalently bound to the DEAE membrane. After the desired fragment was bound to the DEAE membrane, the membrane was removed and rinsed with low salt buffer (150 mM NaCl; 0.1 mM EDTA; and 20 mM Tris-HCl, pH=8). Next, the membrane was placed in a small tube and immersed in high salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer was collected and the membrane rinsed with high salt buffer. The rinse solution was pooled with the incubation buffer before collecting the desired DNA fragments.

About three volumes of cold, absolute ethanol were added to the high salt-DNA solution. The resulting solution was mixed and placed at −70° C. for 10–20 minutes. The solution was chilled and centrifuged at 15,000 rpm for 15 minutes. After another precipitation to remove residual salt, the DNA pellet was rinsed with ethanol, dried, resuspended in 50 μl of TE buffer, and constituted ~2.5 μg of the desired ~3.0 kb PstI restriction fragment of plasmid pOJ159.

About 2 μl (~0.2 μg) of the PstI-digested plasmid pIJ702 DNA were added to 10 μl (~0.5 μg) of the ~3.0 kb, carB-containing PstI restriction fragment of plasmid pOJ159, 2 μl of 10X ligase buffer (660 mM Tris-HCl, pH=8; 66 mM MgCl₂; 10 mM dithiothreitol (DTT); and 10 mM ATP), and 5 μl of H₂O. About 1 μl (~100 units) of T4 DNA ligase was added to the solution of DNA, and the resulting reaction was incubated at 15° C. overnight (~16 hours). The ligated DNA constituted the desired plasmids pOJ169 and pOJ170, which differ only with respect to the orientation of the ~3.0 kb fragment. A restriction site and function map of plasmid pOJ169 is presented in FIG. 2 of the accompanying drawings. The ligated DNA can be used to transform *Streptomyces lividans* TK23 and *Streptomyces griseofuscus* C581 as described in Example 3, below.

EXAMPLE 3

Construction of Carbomycin-Resistant *Streptomyces lividans* TK23 and *S. grisoefuscus* C581

A. List of Solutions

The following solutions are referred to throughout the Examples and are presented here for clarity.

1. P medium (~100 ml):

| Ingredient | Amount |
   | --- | --- |
   | Sucrose | 10.3 g |
   | K₂SO₄ | 0.025 g |
   | Trace element solution (see #3) | 0.2 ml |
   | MgCl₂.6H₂O | 0.203 g |
   | Water | 80 ml |
   | After autoclaving add: | |
   | KH₂PO₄ (0.5%) | 1 ml |
   | CaCl₂.2H₂O (3.68%) | 10 ml |
   | (N-tris-(hydroxymethyl)-methyl-2-aminoethane sulphonic acid), "TES" buffer, 0.25 M, pH = 7.2 | 10 ml |

2. Trace element solution (~1 L):

| Ingredient | Amount |
   | --- | --- |
   | ZnCl₂ | 40 mg |
   | FeCl₃.6H₂O | 200 mg |
   | CuCl₂.2H₂O | 10 mg |
   | MnCl₂.4H₂O | 10 mg |
   | Na₂B₄O₇.10H₂O | 10 mg |
   | (NH₄)₆Mo₇O₂₄.4H₂O | 10 mg |
   | H₂O | 1 L |

3. R2 Regeneration Medium (~1 L):

| Ingredient | Amount |
   | --- | --- |
   | Sucrose | 103 g |
   | K₂SO₄ | 0.25 g |
   | Trace element solution | 2 ml |
   | MgCl₂.6H₂O | 10.12 g |
   | glucose | 10 g |
   | L-asparagine.1H₂O | 2.0 g |
   | casamino acids | 0.1 g |
   | Agar | 22 g |
   | Water | to 700 ml |

The pH is adjusted to pH = 7.2 before autoclaving. After autoclaving, add:

| | |
   | --- | --- |
   | KH₂PO₄ (0.05 g/100 ml) | 100 ml |
   | CaCl₂ (2.22 g/100 ml) | 100 ml |
   | TES Buffer (5.73 g/100 ml, pH = 7.2) | 100 ml |

4. Soft nutrient agar (SNA, ~1 L):

| Ingredient | Amount |
   | --- | --- |
   | Difco Bacto Nutrient Broth | 8 g |
   | Agar | 5 g |

5. R2YE medium is R2 medium with 20 ml of 25% yeast extract added per liter.

6. Yeast Extract - Malt Extract (YEME, ~1 L):

| Ingredient | Amount |
   | --- | --- |
   | Yeast extract | 3 g |
   | Peptone | 5 g |
   | Malt extract | 3 g |
   | Glucose | 10 g |

7. YEME + 34% Sucrose Liquid Complete Medium is YEME with 340 g/L of sucrose.

8. YMX Media (~1 L):

| Ingredient | Amount |
   | --- | --- |
   | Yeast extract | 3 g |
   | Malt extract | 3 g |
   | Glucose | 2 g |
   | Agar | 20 g |

9. YMX Agar is 0.3% yeast extract, 0.3% malt extract, 0.2% dextrose, and 2.0% agar.

B. Transformation of *Streptomyces griseofuscus*

Plasmid pOJ159 was first isolated by transforming a library of MboI-digested *Streptomyces thermotolerans* (ATCC 11416) DNA cloned into BglII-digested plasmid pIJ702 DNA into *S. griseofuscus* C581 (ATCC 23916). A number of thiostrepton-resistant transformants were isolated, homogenized, grown in media containing 0.5 μg/ml carbomycin for about 16 hours, and, finally, plated on media containing 10 μg/ml carbomycin. The transforming DNA was prepared from the carbomycin-resistant transformants in substantial accordance with the procedure of Example 1. The isolated DNA, which included plasmid pOJ159, was then used to transform *S. lividans* TK23 (NRRL 15826) to carbomycin resistance. A similar procedure was used with the ligated DNA prepared in Example 2 to obtain *S. griseofuscus* C581/pOJ169 and *S. griseofuscus* C581/pOJ170 transformants.

*Streptomyces griseofuscus* C581 (ATCC 23916) was plated on YMX agar and incubated at 30° C. for about 72 hours. A plug of cells was removed from the plate and used to inoculate 10 ml of TSB. The culture was homogenized and incubated at 30° C. for ~30 hours. About 4 ml of this culture were homogenized and used to inoculate 100 ml of TSB containing 0.4% glycine. The culture was incubated at 30° C. for about ~24 hours. About 4 ml of this culture were again homogenized and used to inoculate 100 ml of TSB containing 0.4% glycine. The culture was incubated at 30° C. for about 16 hours. The cells were harvested and washed three times with 10.3% sucrose. The cells were resuspended in 100 ml of P media containing 1 mg/ml lysozyme, and the resulting solution was incubated at 30° C. for 2 hours. During this protoplasting step, the cells were pipetted up and down to disperse clumps. The protoplasts were collected and washed three times with P medium. The protoplasts were then suspended in 10 ml of P medium. This process usually generates about 2 to $5 \times 10^7$ protoplasts per 150 $\mu$l of solution.

Approximately 150 $\mu$l of the protoplast solution were added to 10 $\mu$l of the transforming DNA, either in ligation or TE buffer, and mixed. About 101 $\mu$l of 50% polyethylene glycol 1000 in P media were then added and mixed. After a brief (1 to 2 minutes) incubation at room temperature, the cell-DNA mixture was brought to a volume of 1 ml by the addition of P media. The cell suspension was plated onto R2 medium; about 0.1 ml of cells was inoculated per R2 plate. The plates were incubated at 30° C. overnight (~16 hours) and then overlaid with ~3 ml of R2-modified agar (103 g sucrose,; 10.12 g MgCl$_2$; 2.22 g CaCl$_2$; and 5.72 g TES at pH=7.2 per liter) containing enough thiostrepton to give a final concentration, after diffusion, of 25 $\mu$g/ml. The plates were then incubated for about four days at 30° C., when colonies became visible to the naked eye.

Carbomycin-resistant transformants were selected by patching regenerated protoplasts to R2 medium containing 10 $\mu$g/ml of carbomycin. Alternatively, carbomycin-resistant transformants were selected by inoculating the regenerated protoplasts into TSB containing 0.5 $\mu$g/ml carbomycin. The culture was incubated for 16-22 hours at 30° C. before plating the cells onto media containing 10 $\mu$g/ml carbomycin. As plasmids pOJ159, pOJ169, and pOJ170 also comprise a thiostrepton resistance-conferring gene, thiostrepton, at a final concentration of 20 $\mu$g/ml, was also used to select transformants.

The transformants were cultured on R2 agar supplemented with carbomycin (10 $\mu$g/ml) to obtain single colonies. These single colonies were used to inoculate 10 ml TSB cultures containing both carbomycin and thiostrepton (25 $\mu$g/ml). The cultures were homogenized and then grown overnight at 30° C. in a rotary shaker.

Plasmid isolation for analysis was done by a small-scale version of the protocol of Example 1; the CsCl gradients of Example 1 were replaced by ethanol precipitations. The mycelium was collected by centrifugation, washed twice with 10.3% sucrose and then suspended in 1-2 ml of 10.3% sucrose. Four hundred $\mu$l of the cell mixture were transferred to a small tube, and 100 $\mu$l of 5X Lysozyme solution (Example 1) were added. The suspension was incubated at 30° C. for 30-60 minutes, followed by the addition and mixing of 300 $\mu$l of 0.3M NaOH containing 1% SDS. The latter solution was kept at 50° C. before its addition to the cell mix. The cell mixture was placed at 80° C. for 10 minutes, cooled to room temperature, and then extracted with 200 $\mu$l of phenol:CHCl$_3$ (50:50). The aqueous phase was transferred to a clean tube, made 0.3M in NaOAc, and then, one volume of isopropanol was added. The DNA was incubated at room temperature for five minutes and then pelleted by centrifugation. The pellet was dissolved in 500 $\mu$l of TE buffer, and about 25 $\mu$l of 0.1M spermine were added to the solution of DNA, and the mixture was incubated at room temperature for 5 minutes. After centrifugation, the DNA pellet was rinsed with 75% ethanol, then resuspended and reprecipitated from 0.3M sodium acetate using ethanol. After this last precipitation, the plasmid DNA was suspended in 50 $\mu$l of TE buffer. Restriction enzyme cutting and electrophoretic analysis of the reaction products were used to determine plasmid structure.

C. Preparation of *Streptomyces lividans* Protoplasts and Transformation to Carbomycin Resistance

*Streptomyces lividans* TK23 (NRRL 15826) was plated on R2 agar, and the plates were incubated at 30° C. for 16 hours. A plug of cells was taken from the plate and used to inoculate 10 ml of TSS-glycine (12% sucrose and 0.5% glycine in TSB). This culture was incubated at 30° C. for ~65 hours with aeration. The culture was then homogenized, sonicated, pelleted with centrifugation, and washed with 10 ml of P media. The cell pellet was resuspended in P media containing 2 mg/ml lysozyme, incubated at 4° C. for 15 minutes, mixed by inversion, and then incubated at 4° C. for 30 minutes. The resulting protoplasts were washed twice in P media and then resuspended in 10 ml of P media. For each sample of transforming DNA (~5 $\mu$l), 200 $\mu$l of protoplasts were added to the DNA together with 0.5 ml of 20% polyethylene glycol 1000 in P media. The cells were then plated in 200 $\mu$l aliquots using ~3 ml of R2-modified overlays (103 g sucrose, 10.12 g MgCl$_2$, 2.22 g CaCl$_2$, and 5.73 g TES at pH=7.2 per liter). The plates were incubated at 30° C.

Thiostrepton and carbomycin were added and transformants identified as described for the preparation of *Streptomyces griseofuscus* transformants. *Streptomyces lividans* TK23/pOJ159 transformants were prepared in accordance with the preceding procedure.

We claim:

1. A method for selecting a recombinant DNA-containing host cell that comprises transforming a carbomycin-sensitive actinanyceles host cell with a recombinant DNA vector that codes for the carB gene product and culturing the transformed cell under conditions suitable for selection of carbomycin-resistant transformants.

2. The method of claim 1 wherein said host cell is Streptomyces.

3. The method of claim 2 wherein said host cell is *Streptomyces griseofuscus*.

4. The method of claim 2 wherein said host cell is *Streptomyces lividans*.

5. A recombinant DNA that encodes the carB gene product of the method of claim 1.

6. The DNA of claim 5 that comprises the carB gene of *Streptomyces thermotolerans*.

7. The DNA of claim 5 that comprises the sequence:

```
5'-ATG GCC GCA GCG CGT ACA ACC GGA GCT
CAG TCG CGT AAA ACG GCA CAG CGG TCG GGC
CGG AGT GAG GCT GAC CGT
AGA AGA AGA GTC CAC GGG CAG AAT TTC CTC GTC
GAC CGG GAA ACA GTA
CAA CGG TTT GTG CGT TTC GCC GAT CCG GAC CCC
GGG GAG GTC GTT CTC
GAG GTC GGT GCC GGT AAT GGT GCG ATC ACG CGC
GAG CTG GCG CGA TTA
TGC CGA CGA GTG GTG GCG TAT GAG ATC GAC
CGG CAC TTC GCG GAC CGA
TTA CGT GAG GCG ACC GCC GAG GAT CCG CGG ATC
GAG GTC GTC GCC GGC
GAC TTC CTG AAG ACC TCG CAG CCC AAG GTC CCG
TTC TCC GTG GTC GGC
AAC ATC CCG TTC GGC AAC ACC GCG GAC ATA GTG
GAC TGG TGC CTG AAC
GCG CGG CGG CTG CGT ACG ACC ACC CTG GTC
ACC CAG CTC GAA TAC GCC
CGC AAG CGC ACC GGC GGC TAT CGG CGC TGG TCA
CGG CTC ACC GTG GCC
ACC TGG CCC GAG GTG GAG TGG CGG ATG GGC
GAG CGG ATC AGC CGC CGG
TGG TTC CGG CCC GTC CCC GCC GTC GAC TCC GCG
GTA CTG CGA CTG GAA
CGG CGA CCG GTG CCG CTG ATC CCA CCC GGT CTG
ATG CAC GAC TTC CGG
GAC CTG GTG GAG ACC GGG TTC ACG GGA AAG
GGC GGT TCG CTG GAC GCC
TCG CTG CGC CGG CGC TTC CCG GCC CGG CGG GTG
GCC GCC GGG TTC CGC
AGG GCC CGC CTG GAG CAG GGC GTG GTC GTC GCC
TAC GTC ACC CCG GGC
CAA TGG ATC ACA CTC TTC GAG
GAA CTC CAC GGG CGC-3'
``` wherein A is deoxyadenyl, G is deoxyguanyl, C is deoxycytidyl, and T is thymidyl.

8. A recombinant DNA vector that comprises the DNA of claim 5.
9. The vector of claim 8 that is a plasmid.
10. The plasmid of claim 9 that is plasmid pOJ159.
11. The plasmid of claim 9 that is plasmid pOJ169.
12. The plasmid of claim 9 that is plasmid pOJ170.
13. The plasmid of claim 9 that is plasmid pOJ168.
14. The plasmid of claim 9 that is plasmid pOJ168.1.
15. A host cell transformed with a recombinant DNA vector of claim 8.
16. The host cell of claim 15 that is Streptomyces.
17. The host cell of claim 15 that is *Streptomyces lividans*.
18. The host cell of claim 15 that is *Streptomyces griseofuscus*.
19. The host cell of claim 17 that is *Streptomyces lividans*/pOJ159.
20. The host cell of claim 17 that is *Streptomyces lividans*/pOJ169.
21. The host cell of claim 17 that is *Streptomyces lividans*/pOJ170.
22. The host cell of claim 18 that is *Streptomyces griseofuscus*/pOJ159.
23. The host cell of claim 18 that is *Streptomyces griseofuscus*/pOJ169.
24. The host cell of claim 18 that is *Streptomyces griseofuscus*/pOJ170.
25. An isolated and purified DNA sequence as follows:

```
5'-TGA CGCACAC CGGTGCGGGG
    CGCGCCCGAG GGCGCGCCCC
    GCACCGGTCG TCCC-3'
``` wherein A is deoxyadenyl, G is deoxyguanyl, C is deoxycytidyl, and T is thymidyl.

* * * * *

UNITED STATES PATENT AND TRADEMARK OFFICE
CERTIFICATE OF CORRECTION

PATENT NO. : 4,914,030

DATED : April 3, 1990

INVENTOR(S) : Schoner et al.

It is certified that error appears in the above-identified patent and that said Letters Patent is hereby corrected as shown below:

In Column 22, line 54, change "actinanyceles" to -- actinomycetes --.

In Column 23, line 23 of the sequence, change "AGC CGC CGG" to -- AGC CGC CGC --.

Signed and Sealed this

Fourth Day of February, 1992

Attest:

HARRY F. MANBECK, JR.

*Attesting Officer*      *Commissioner of Patents and Trademarks*